United States Patent [19]

Liebl et al.

[11] Patent Number: 4,838,931
[45] Date of Patent: Jun. 13, 1989

[54] 1,2-DISUBSTITUTED PIPERIDINES, PROCESSES FOR THEIR PREPARATION AND THEIR USE IN PLANT PROTECTION

[75] Inventors: Rainer Liebl, Todtenweis; Michael Frey, Gersthofen; Hilmar Mildenberger, Kelkheim; Klaus Bauer, Rodgau; Hermann Bieringer, Eppstein/Taunus, all of Fed. Rep. of Germany

[73] Assignee: Hoechst Aktiengesellschaft, Frankfurt, Fed. Rep. of Germany

[21] Appl. No.: 3,202

[22] Filed: Jan. 14, 1987

[30] Foreign Application Priority Data

Jan. 16, 1986 [DE] Fed. Rep. of Germany ....... 3601048

[51] Int. Cl.$^4$ ............... A01N 43/40; C07D 211/22
[52] U.S. Cl. ............................. 71/94; 71/86; 71/87; 546/22; 546/205; 546/206; 546/226
[58] Field of Search .................. 546/226; 71/94

[56] References Cited

U.S. PATENT DOCUMENTS

| | | | |
|---|---|---|---|
| 3,505,340 | 4/1970 | Frey et al. | 546/226 X |
| 3,758,481 | 9/1973 | Hya et al. | 546/226 |
| 3,787,393 | 1/1974 | Aya et al. | 546/226 X |
| 3,956,296 | 5/1976 | Duncan, Jr. et al. | 546/189 X |
| 3,972,707 | 8/1976 | Muller et al. | 546/226 X |
| 3,988,300 | 10/1976 | Cross | 546/226 X |
| 4,032,642 | 6/1977 | Duncan, Jr. et al. | 514/234 |
| 4,068,079 | 1/1978 | Gaughan | 546/226 X |
| 4,323,388 | 4/1982 | Pissiotas et al. | 546/226 X |
| 4,437,877 | 3/1984 | Nagano et al. | 546/226 X |
| 4,499,100 | 2/1985 | Kluge et al. | 514/821 X |

OTHER PUBLICATIONS

Environmental Quality Safety Suppl. (Pesticides) vol. 3, p. 696 (1975).

*Primary Examiner*—Joseph P. Brust
*Attorney, Agent, or Firm*—Curtis, Morris & Safford

[57] ABSTRACT

1,2-Disubstituted piperidines of the general formula I

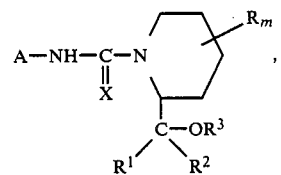

in which X denotes oxygen or sulfur; R denotes alkyl, $R^1$ and $R^2$ denote hydrogen, alkyl or benzyl, $R^3$ denotes hydrogen, (substituted) alkyl, (substituted) benzyl or a radical of the formulae

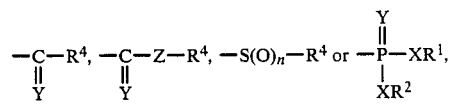

Y and X denote S or O; Z denotes S, O or $NR^1$; $R^4$ denotes hydrogen, (substituted) alkyl, (substituted) phenyl, (substituted) naphthyl or (substituted) pyridyl, A denotes (substituted) phenyl or (substituted) naphthyl and m denotes 0, 1 or 2, possess advantageous herbicidal properties.

5 Claims, No Drawings

1,2-DISUBSTITUTED PIPERIDINES, PROCESSES FOR THEIR PREPARATION AND THEIR USE IN PLANT PROTECTION

Cyclic urea compound containing piperidine and having herbicidal activity are disclosed in Environmental Quality and Safety Suppl. (Pesticides) volume 3, page 696 (1975). The herbicidal action of these is, however, inadequate. The present invention relates to new 1,2-disubstituted piperidines of the general formula I

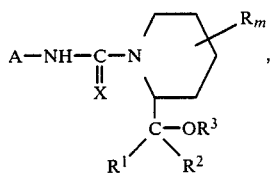

in which
X denotes oxygen or sulfur;
R denotes $(C_1-C_4)$-alkyl,
$R^1$, $R^2$ independently of one another denote hydrogen, $(C_1-C_4)$-alkyl or phenyl or benzyl, both of which can be monosubstituted to trisubstituted by $(C_1-C_4)$-alkyl, halogen, $CF_3$, $NO_2$ or CN,
$R^3$ denotes hydrogen, $(C_1-C_4)$-alkyl which is unsubstituted or monosubstituted to trisubstituted by halogen, $(C_3-C_6)$-cycloalkyl, $(C_3-C_4)$-alkenyl, $(C_5-C_6)$-cycloalkenyl, $(C_3-C_4)$-alkynyl, $(C_1-C_4)$-alkoxy-$(C_1-C_4)$-alkyl or $(C_1-C_4)$-alkoxycarbonyl-$(C_1-C_4)$-alkyl; phenyl or benzyl, both of which are unsubstituted or monosubstituted to trisubstituted by halogen, $(C_1-C_4)$-alkyl, $NO_2$, $CF_3$, $(C_1-C_4)$-alkoxy or $(C_1-C_4)$-alkoxycarbonyl; or a radical of the formulae

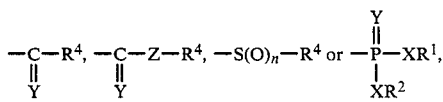

Y denotes oxygen or sulfur,
Z denotes oxygen, sulfur or $-NR^1$,
$R^4$ denotes hydrogen, $(C_1-C_8)$-alkyl which is unsubstituted or monosubstituted to trisubstituted by halogen, or phenyl or benzyl, both of which are unsubstituted or monosubstituted to trisubstituted on the aromatic ring by halogen, $(C_1-C_4)$-alkyl, $(C_1-C_4)$-alkoxy, $(C_1-C_4)$-alkoxycarbonyl, $NO_2$, $CF_3$ or CN,
m denotes 0, 1 or 2,
n denotes 1 or 2, and
A denotes phenyl or naphthyl, both of which are unsubstituted or monosubstituted to tetrasubstituted by halogen, $(C_1-C_4)$-alkyl, $(C_1-C_4)$-halogenoalkyl, $(C_1-C_4)$-alkoxy, $(C_1-C_4)$-halogenoalkoxy, $(C_3-C_6)$-cycloalkoxy, $(C_2-C_4)$-alkenyloxy, $(C_2-C_4)$-halogenoalkenyloxy, $(C_5-C_6)$-cycloalkenyloxy, $(C_3-C_4)$-alkynyloxy, $(C_3-C_4)$-halogenoalkynyloxy, $(C_1-C_4)$-alkoxy-$(C_1-C_4)$-alkoxy, $(C_1-C_4)$-alkoxycarbonyl, $(C_1-C_4)$-alkoxycarbonyl-$(C_1-C_4)$-alkoxy, $(C_1-C_4)$-alkoxycarbonyl-$(C_1-C_4)$-alkoxycarbonyl, $(C_1-C_4)$-alkylthio, $(C_1-C_4)$-alkylsulfinyl, $(C_1-C_4)$-alkylsulfonyl, $(C_1-C_4)$-alkoxycarbonyl-$(C_1-C_4)$-alkylthio or phenoxy, benzyloxy or phenoxymethyl, it being possible for the three radicals last mentioned to be monosubstituted or disubstituted in the phenyl ring by halogen, $CF_3$ or $(C_1-C_4)$-alkyl, or A denotes $NO_2$, $CF_3$, CN or pyridyl which is unsubstituted or monosubstituted to trisubstituted by halogen, $(C_1-C_4)$-alkyl, $NO_2$, $CF_3$ or $(C_1-C_4)$-alkoxy.

Preferred compounds are those in which R denotes $(C_1-C_4)$-alkyl,
$R^1$ and $R^2$ independently of one another denote hydrogen or $(C_1-C_4)$-alkyl,
$R^3$ denotes hydrogen, $(C_1-C_4)$-alkyl,

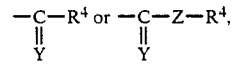

$R^4$ denotes $(C_1-C_4)$-alkyl, or phenyl which is unsubstituted or monosubstituted or disubstituted by halogen, $(C_1-C_4)$-alkyl or $CF_3$,
A denotes phenyl which is monosubstituted to trisubstituted by halogen, $(C_1-C_4)$-alkoxy, $(C_1-C_4)$-halogenoalkoxy, $(C_1-C_4)$-alkylthio,$(C_1-C_4)$-alkylsulfonyl, propargyloxy, $(C_1-C_4)$-alkoxycarbonyl or $(C_1-C_4)$-alkyloxycarbonyl$(C_1-C_4)$-alkoxy, and
m denotes 0 or 1.

Compounds of the formula I which are particularly preferred are those in which R denotes $(C_1-C_4)$-alkyl; $R^1$ and $R^2$ denote H or $(C_1-C_4)$-alkyl, $R^3$ denotes H, $(C_1-C_4)$-alkyl or $-CO(C_1-C_4$-alkyl$)$ and A denotes a phenyl radical which is monosubstituted to trisubstituted by F, Cl, Br, $(C_1-C_4)$-alkoxy, $(C_1-C_4)$-alkoxycarbonyl-$(C_1-C_4)$-alkoxy or propargyloxy, the radicals being located, in particular, in the 2-, 4- or 5-position in the phenyl radical.

The term halogenoalkyl, halogenoalkoxy, halogenoalkenyl or halogenoalkynyl denotes in each case an alkyl, alkoxy, alkenyl or alkynyl radical which is monosubstituted or polysubstituted by halogen, in particular F, Cl or Br. Halogenoalkyl is to be understood as meaning, for example, $CF_3$, $C_2F_5$, $CF_2Cl$, $CF_2CHF_2$, $CH_2CF_3$, $CF_2CHFCl$, $CF_2CHFCF_3$ or $CF_2CHFBr$. Halogenoalkoxy embraces, for example, the radicals $OCF_3$, $OCF_2CHF_2$, $OCF_2CHFCl$, $OCF_2CHCl_2$, $OCF_2CHBr$ or $OCF_2-CHF-CF_3$.

The compounds of the formula I possess one or more centers of asymmetry in the piperidine ring and can therefore exist in the form of pure optical isomers, diastereomers or mixtures thereof. Formula I embraces all these isomers or mixtures of isomers.

The present invention also relates to processes for the preparation of compounds of the general formula I, which comprise
(a) reacting a compound of the formula II with a piperidine derivative of the formula III

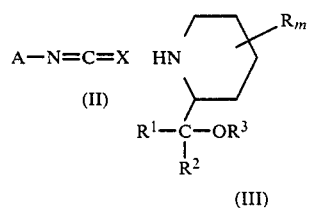

or
(b) reacting an amine of the formula IV in the presence of a base with a compound of the formula V

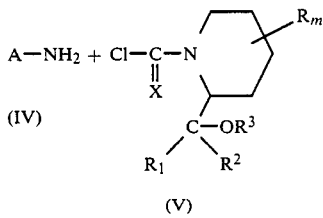

and, if appropriate, O-alkylating or O-acylating the compounds of the formula I in which $R^3 = H$ obtained under (a) or (b).

Process variant (a) is carried out in an organic solvent, such as, for example, ether, tetrahydrofuran, toluene, acetone, acetonitrile, methylene chloride or chloroform. In variant (b) the base employed can be an inorganic base, such as an alkali metal hydroxide or carbonate, or an organic base, such as an organic amine, for example pyridine or triethylamine. This reaction too is carried out in an organic solvent which is inert under the conditions of the reaction.

The isocyanates or isothiocyanates of the formula II and also the amines of the formula IV are known or can be prepared by methods with which those skilled in the art are familiar, see Houben Weyl, Methoden der Organischen Chemie, ("Methods of Organic Chemistry"), volume VIII, page 120, Georg Thieme Verlag Stuttgart; or Houben Weyl, Volume IX, pages 875 and 869. The piperidines of the formula III and the carbamoyl chlorides of the formula V are in part known or can be prepared from 2-hydroxyalkylpiperidines by known methods of synthesis, cf. J. Am. Chem. Soc. 77 (1955), 29, J. Am. Chem. Soc. 69 (1947), 3039, J. Am Chem. Soc. 61 (1939), 638; Soc. 1949, 2095.

The alkylation or acylation of the compounds of the formula I in which $R^3 = H$ is carried out by methods with which those skilled in the art are familiar, see, for example, Organikum, 15th edition, page 253 and 505, VEB Verlag, Berlin.

The compounds, according to the invention, of formula I display an excellent herbicidal activity against a broad spectrum of monocotyledonous and dicotyledonous weeds of economic importance. Even perennial weeds which are difficult to control and sprout from rhizomes, root-stocks or other long-lasting organs are thoroughly dealt with by the active compounds. It is immaterial in this regard whether the substances are applied by the pre-sowing, pre-emergence or post-emergence technique.

If the compounds according to the invention are applied to the surface of the soil before germination, either the emergence of the weed seedlings is completely prevented or the weeds grown until they reach the cotyledon stage but then cease growing and finally wither completely after the expiration of three to five weeks. If the active compounds are applied to the green parts of the plants by the post-emergence technique, a drastic cessation of growth also takes place very rapidly after the treatment and the weed plants remain in the stage of growth existing at the time of application or wither completely at varying rates after a certain time, so that weed competition harmful to the crop plants can be eliminated in this way very soon and in a lasting manner by the use of the new agents according to the invention.

Although the compounds according to the invention display an excellent herbicidal activity against monocotyledonous and dicotyledonous weeds, crop plants belonging to crops of economic importance, such as, for example, wheat, barley, rye, rice, maize, sugar beet, cottom and soya, are damaged only insubstantially or not at all. For these reasons, the present compounds are very suitable for selectively controlling undesirable plant growth in agricultural plantations.

In addition, the compounds according to the invention display growth-regulating properties with crop plants. They intervene in a regulatory manner in the plant's metabolism and can thus be employed for facilitating harvesting, for example by initiating desiccation, abscission and inhibition of growth. They are also suitable for the general control and inhibition of undesired vegetative growth, without thereby killing the plants. In the case of many monocotyledonous and dicotyledonous crops inhibition of vegetative growth plays an important part, since it is possible thereby to reduce, or completely prevent, lodging.

The agents according to the invention can be used in the form of wettable powders, emulsifiable concentrates, sprayable solutions, dusting agents, dressing agents, dispersions, granules or microgranules in the customary formulations.

Wettable powders are preparations which can be dispersed uniformly in water and which, besides the active compound and, if appropriate, a diluent or inert substance, also contain wetting agents, for example polyoxethylated alkyl phenols, polyoxethylated fatty alcohols, alkylsulfonates or alkylphenylsulfonates, and dispersing agents, for example sodium ligninsulfonate, sodium 2,2'-dinaphthylmethane-6,6'-disulfonate, sodium dibutylnaphthalenesulfonate or sodium oleoylmethyltauride. Preparation is carried out in a customary manner, for example by grinding and mixing the components.

Emulsifiable concentrates can be prepared, for example, by dissolving the active compound in an inert organic solvent, for example butanol, cyclohexanone, dimethylformamide, xylene or higher-boiling aromatic compounds or hydrocarbons with the addition of one or more emulsifiers. In the case of liquid active compounds the solvent component can also be wholly or partially omitted. The following, for example, can be used as emulsifiers: calcium alkylarylsulfonates, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxethylenesorbitan fatty acid esters of polyoxethylenesorbitol esters.

Dusting agents can be obtained by grinding the active compound with finely divided solid substances, for example talc, natural clays, such as kaolin, bentonite or pyrophillite, or diatomaceous earth.

Granules can be prepared either by atomizing the active compound onto adsorptive, granulated inert material or by applying concentrations of active compound by means of binders, for example polyvinyl alcohol, sodium polyacrylate or mineral oils, to the surface of carriers, such as sand, kaolinite or granulated inert material. It is also possible to granulate suitable active compounds in the manner customary for the production of fertilizer granules, if desired as a mixture with fertilizers.

In wettable powders the concentration of active compound is, for example, about 10 to 90% by weight, the remaining up to 100% by weight being composed of customary formulation ingredients. In the case of emulsifiable concentrates the concentration of active compound can be about 5 to 80% by weight. Formulations in the form of dusts contain in most cases 5 to 20% by weight of active compound; sprayable solutions contain about 2 to 20% by weight. In the case of granules the content of active compound depends in part on whether the active compound is in a liquid or solid form and on the granulating auxiliaries, fillers and the like which are used.

In addition, the formulations of active compounds mentioned contain, if appropriate, the tackifiers, wetting agents, dispersing agents, emulsifiers, penetration agents, solvents, fillers or carriers which are customary in the particular case.

For application, the concentrates which are in the form customary in commerce are optionally diluted in a customary manner, for example with water in the case of wettable powders, emulsifiable concentrates and dispersions and, in part, also in the case of microgranules. Formulations in the form of dusts and granules and also sprayable solutions are usually not diluted further with additional inert substances before being used.

The application rate required varies with the external conditions such as temperature, humidity and others. It can vary within wide limits, for example between 0.005 and 10.0 kg/hectare or more of active substance, but is preferably between 0.01 and 5 kg/hectare.

Mixtures or mixed formulations with other active compounds, such as, for example, insecticides, acaricides, herbicides, fertilizers, growth regulators or fungicides, are also possible in certain cases.

The invention is illustrated in greater detail by means of the examples below.

FORMULATION EXAMPLES

A. A dusting agent is obtained by mixing 10 parts by weight of active compound and 90 parts by weight of talc or an inert substance and comminuting the mixture in a beater mill.

B. A wettable powder which is readily dispersible in water is obtained by mixing 25 parts by weight of active compound, 64 parts by weight of kaolin-containing quartz, as inert substance, 10 parts by weight of potassium ligninsulfonate and 1 part by weight of sodium oleoylmethyltauride, as a wetting and dispersing agent, and grinding the mixture in a pinned disk mill.

C. A dispersion concentrate which is readily dispersible in water is obtained by mixing 20 parts by weight of active compound with 6 parts by weight of alkylphenol polyglycol ether (Triton X 207), 3 parts by weight of isotridecanol polyglycol ether (8 EO) and 71 parts by weight of paraffinic mineral oil (boiling range approx. 255° to over 377° C., for example), and grinding the mixture in a ball mill to a fineness of less than 5 microns.

D. An emulsifiable concentrate is obtained from 15 parts by weight of active compound, 75 parts by weight of cyclohexanone, as solvent, and 10 parts by weight of oxethylated nonylphenol (10 EO), as emulsifier.

CHEMICAL EXAMPLES

EXAMPLE 1

1-[N-(4-chloro-2-fluoro-5-methoxyphenyl)-carbamoyl]-2-hydroxymethylpiperidine 10.1 g (0.05 mol) of 4-chloro-2-fluoro-5-methoxyphenyl isocyanate are dissolved in 50 ml of toluene, and 5.8 g (0.05 mol) of 2-hydroxymethylpiperidine, dissolved in 20 ml of toluene, are added dropwise at RT$^{(1)}$. The mixture is stirred for 2 hours at 20°–25° C. and cooled in and ice bath, and the precipitate which has been deposited is filtered off with suction. 12.6 g (79% of theory) of 1-[N-(4-chlor-2-fluor-5-methoxyphenyl)-carbamoyl]-2-hydroxymethylpiperidine are obtained after drying in the form of colorless crystals, melting point 176°–179° C.

EXAMPLE 2

2-hydroxymethyl-1-{N-[3-methyl-4-(1,1,2,2-tetrafluoroethoxy)-phenyl]-carbamoyl}-piperidine 11.5 g (0.10 mol) of 2-hydroxymethylpiperidine are dissolved in 100 ml of ether, and 24.9 g (0.10 mol) of 3-methyl-4-(1,1,2,2-tetrafluoroethoxy)-phenyl isocyanate, dissolved in 70 ml of ether, are added dropwise at 20° C. The mixture is stirred for 2 hours at 20° C. and cooled in an ice bath, and the precipitate which has been deposited is filtered off with suction. 32.1 g (88% of theory) of 2-hydroxymethyl-1-{N-[3-methyl-4-(1,1,2,2,-tetrafluoroethoxy)-phenyl]-carbamoyl}-piperidine are obtained after drying, in the form of colorless crystals, melting point 122°–126° C.

EXAMPLE 3

1-[N-(4-chloro-2-fluoro-5-methoxyphenyl)-thiocarbamoyl]-2-hydroxymethylpiperdine 11.5 g (0.10 mol) of 2-hydroxymethylpiperidine are dissolved in 100 ml of ether, and 21.8 g (0.10 mol) of 4-chloro-2-fluoro-5-methoxyphenyl isothiocyanate are added dropwise at RT. The mixture is stirred for 2 hours at 30° C., washed with twice 100 ml of water and dried over sodium sulfate, and the solvent is removed. 32.6 g (98% of theory) of 1-[N-(4-chloro-2-fluoro-5-methoxyphenyl)thiocarbamoyl]-2-hydroxymethylpiperidine are obtained in the form of a pale yellow viscous oil.
$^{(1)}RT = Room\ Temperature$

EXAMPLE 4

2-(N-Methylcarbamoyloxymethyl)-1-{N-[3-methyl-4-(1,1,2,2-tetrafluoroethoxy)-phenyl]carbamoyl}-piperdine 18.2 g (0.05 mol) of 2-hydroxymethyl-1-{N-[3-methyl-4-(1,1,2,2,-tetrafluoroethoxy)-phenyl]carbamoyl}-piperidine from Example 2 are dissolved in 100 ml of acetonitrile, and 3.4 g (0.06 mol) of methyl isocyanate are added dropwise at 20° C. 50 mg of diazabicyclo[2.2.2]nonane are added and the mixture is stirred for 1 hour at 20° C. and for 4 hours at 50° C. The solvent is removed by distillation and the resinous residue is triturated with a 1:1 mixture of ether and hexane. The crystalline precipitate is filtered off with suction and dried. This gives 18.5 g (88% theory) of 2-(N-methylcarbamoyloxymethyl)-1-{N-[3-methyl-4-(1,1,2,2-tetrafluoroethoxy)phenyl]-carbamoyl}-piperidine in the form of colorless crystals, melting point 128°–132° C.

EXAMPLE 5

1-[N-(4-Chloro-2-fluoro-5-methoxyphenyl)-carbamoyl]-2-pivaloyloxymethylpiperidine 15.9 g (0.05 mol) of 1-[N-(4-chloro-2-fluoro-5-methoxyphenyl)-carbamoyl]-2-hydroxymethylpiperidine (Example 1) and 4.7 g (0.06 mol) of pyridine are dissolved in 200 ml of toluene, and 6.0 g (0.05 mol) of pivaloyl chloride are added dropwise at 20° C. The mixture is stirred for 3 hours at 50° C. and washed with twice 100 ml of water, and the toluene phase is dried over sodium sulfate. After the solvent as been removed, 18.4 g (92% of theory) of 1-[N-(4-chloro-2-fluoro-5-methoxyphenyl)-carbamoyl]-2-pivaloyloxymethyl-piperidine are obtained in the form of a colorless viscous oil.

EXAMPLE 6

1-[N-(4-chloro-2-fluoro-5-methoxyphenyl)-carbamoyl]-2-ethoxycarbonyloxymethylpiperidine 15.9 g (0.05 mol) of 1-[N-(4-chloro-2-fluoro-5-methoxyphenyl)-carbamoyl]-2-hydroxymethylpiperidine (Example 2) and 6.0 g (0.06 mol) of triethylamine are dissolved in 150 ml of toluene, and 5.4 g (0.05 mol) of ethylchloroformate are added dropwise at 20° C. The mixture is stirred for 2 hours at 40° C. and washed with twice 50 ml of water, and the toluene phase is dried over sodium sulfate. After the solvent has been removed, 19.0 g (97% of theory) of 1-[N-(4-chloro-2-fluoro-5-methoxyphenyl)-carbamoyl]-2-ethoxycarbonyloxymethylpiperidine are obtained in the form of a viscous, pale yellow oil.

The compounds in Table I are obtained in a manner analogous to that described in Examples 1-6.

TABLE I

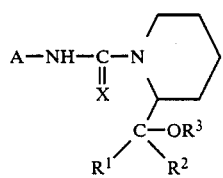

| Example | $R^1$ | $R^2$ | $R^3$ | X | A | M.p. [°C.] |
|---|---|---|---|---|---|---|
| 7 | H | H | H | O | 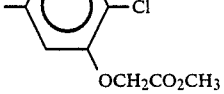 | Resin |
| 8 | H | H | H | O | 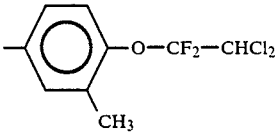 | |
| 9 | H | H | H | O | 3-$CF_3$—4-$OC_2H_5$—$C_6H_3$ | 168–170 |
| 10 | H | H | H | O | 4-Cl—$C_6H_4$ | 125–127 |
| 11 | H | H | H | O | 4-Br—$C_6H_4$ | 132–138 |
| 12 | H | H | H | O | 4-i-$C_3H_7$—$C_6H_4$ | Resin |
| 13 | H | H | H | O | 3,4-$Cl_2$—$C_6H_3$ | |
| 14 | H | H | H | O | 3-$CH_3$—4-Cl—$C_6H_3$ | |
| 15 | H | H | H | O | 4-(4-Cl—$C_6H_4O$)—$C_6H_4$ | |
| 16 | H | H | H | O | 2,4-$Cl_2$—5-(—$CO_2C_2H_5$)—$C_6H_2$ | 137–141 |
| 17 | H | H | H | O | 2,4-$F_2$—$C_6H_3$ | |
| 18 | H | H | H | O | 4-F—$C_6H_4$ | |
| 19 | H | H | H | O | 3,5-$Cl_2$—$C_6H_3$ | |
| 20 | H | H | H | O | 4-$CH_3$—3-$OCH_3$—$C_6H_3$ | |
| 21 | H | H | H | O | 3-$CF_3$—$C_6H_4$ | |
| 22 | H | H | H | O | 3-($HF_2C$—$CF_2$—O)—$C_6H_4$ | |
| 23 | H | H | H | O | 3-(ClFHC—$CF_2$—O)—$C_6H_4$ | 102–107 |
| 24 | H | H | H | O | 3-($Cl_2HC$—$CF_2$—O)—$C_6H_4$ | |
| 25 | H | H | H | O | 4-($F_2HC$—$CF_2$—O)—$C_6H_4$ | 104–106 |
| 26 | H | H | H | O | 4-$F_3CO$—$C_6H_4$ | |
| 27 | H | H | H | O | 4-(HC≡C—$CH_2$—O)—$C_6H_4$ | |
| 28 | H | H | H | O | 4-(BrFHC—$CF_2$—O)—$C_6H_4$ | |
| 29 | H | H | H | O | 4-(ClHC=CCl—O)—$C_6H_4$ | |
| 30 | H | H | H | O | 4-($F_3C$—CFH—$CF_2$—O)—$C_6H_4$ | |
| 31 | $CH_3$ | $CH_3$ | H | O | 4-Cl—2-F—5-$OCH_3$—$C_6H_2$ | |
| 32 | " | " | H | O | 4-Cl—$C_6H_4$ | |
| 33 | " | " | H | O | 3-$CF_3$—4-$C_2H_5O$—$C_6H_3$ | |
| 34 | " | " | H | O | 3-$CH_3$—4-($F_2H$—$CF_2$—O)—$C_6H_3$ | |
| 35 | H | H | H | S | 4-Cl—$C_6H_4$ | |
| 36 | H | H | H | S | 3-Cl—4-$CH_3$—$C_6H_3$ | |
| 37 | H | H | H | S | 3,4-$Cl_2$—$C_6H_3$ | |
| 38 | H | H | H | S | 3-$CF_3$—$C_6H_4$ | |
| 39 | H | H | H | S | 3-$CF_3$—4-$C_2H_5O$—$C_6H_3$ | |
| 40 | H | H | H | S | 3-$CH_3$—4-($F_2HC$—$CF_2$—O)—$C_6H_3$ | |

TABLE I-continued

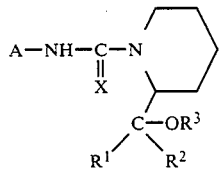

| | $R_1$ | $R_2$ | $R_3$ | X | A | M.p. [°C.] |
|---|---|---|---|---|---|---|
| 41 | H | H | —C(=O)—CH$_3$ | O | 4-Cl—2-F—5-H$_3$CO—C$_6$H$_2$ | |
| 42 | H | H | —C(=O)—NH—CH$_3$ | O | " | |
| 43 | H | H | —C(=O)—CH$_3$ | O | 3-CF$_3$—4-C$_2$H$_5$O—C$_6$H$_3$ | |
| 44 | H | H | —C(=O)—NHCH$_3$ | O | 3-CH$_3$—4-(F$_2$HC—CF$_2$—O)C$_6$H$_3$ | |
| 45 | H | H | H | O | 3-Cl—5-F—2-OCH$_3$—C$_6$F$_2$ | Resin |
| 46 | H | H | H | O | 2,4-Cl$_2$—6-F—3-OCH$_3$—C$_{65}$H | 136–142 |
| Example | $R_1$ | $R_2$ | $R_3$ | X | A | M.p. [°C.] |
| 47 | CH$_3$ | H | CH$_3$ | O | 4-Cl—2F—5-OCH$_3$—C$_6$H$_2$ | Oil |
| 48 | CH$_3$ | CH$_3$ | H | O | 4-Cl—C$_6$H$_4$ | Resin |
| 49 | CH$_3$ | CH$_3$ | H | O | 4-Cl—2-F—5-OCH$_3$—C$_6$H$_2$ | Sirup |
| 50 | H | H | 2-Cl—4-CF$_3$—C$_6$H$_3$ | O | 4-Cl—C$_6$H$_4$ | Resin |
| 51 | H | C$_6$H$_5$ | H | O | 4-Cl—2-F—5-OCH$_3$—C$_6$H$_2$ | 64–68 |
| 52 | H | H | 2-CF$_3$—C$_6$H$_4$ | O | 4-Cl—C$_6$H$_4$ | 137–142 |
| 53 | H | H | CH(C$_6$H$_5$)$_2$ | O | 4-Cl—2-F—5-OCH$_3$—C$_6$H$_2$ | Resin |
| 54 | H | H | C$_2$H$_5$ | O | 4-Cl—2-F—5-OCH$_3$—C$_6$H$_2$ | Sirup |
| 55 | H | C$_6$H$_5$ | C$_6$H$_5$ | O | 4-Cl—2-F—5-OCH$_3$—C$_6$H$_5$ | Sirup |
| 56 | H | CH$_3$ | H | O | 4-Cl—2-F—5-OCH$_3$—C$_6$H$_5$ | Oil |
| 57 | H | C$_2$H$_5$ | 4-CF$_3$—C$_6$H$_4$ | O | 4-Cl—2-F—5-OCH$_3$—C$_6$H$_5$ | Resin |
| 58 | H | H | H | O | 4-Cl—2-F—5-OCH$_2$C=CH—C$_6$H$_2$ | Sirup |
| 59 | H | H | C(O)C(CH$_3$)$_3$ | O | 4-Cl—2-F—5-OCH$_2$C=CH—C$_6$H$_2$ | Sirup |
| 60 | H | H | —H | O | 4-Cl—2-F—5-OCH$_2$C=CH—C$_6$H$_2$ | Resin |
| 61 | H | H | —CO—C(CH$_3$)$_3$ | O | 4-Cl—2-F—5-OCH$_2$C=CH—C$_6$H$_2$ | Resin |
| 62 | H | H | H | O | 4-Cl—2-F—5-[OCH(CH$_3$)CO$_2$C$_2$H$_5$]—C$_6$H$_2$ | Sirup |
| 63 | H | H | —CO—C(CH$_3$)$_3$ | O | 4-Cl—2-F—5-[OCH(CH$_3$)CO$_2$C$_2$H$_5$]—C$_6$H$_2$ | Sirup |
| 64 | H | H | PS(OC$_2$H$_5$))$_2$ | O | 4-Cl—2-F—5-OCH$_3$—C$_6$H$_2$ | Resin |
| 65 | H | H | H | O | 4-Cl—2-F—5-OCH(CH$_3$)$_2$—C$_6$H$_2$ | 144–149 |
| 66 | H | H | CH$_2$—(4-Cl—C$_6$H$_4$) | O | 4-Cl—2-F—5-OCH$_3$—C$_6$H$_2$ | 114–120 |
| 67 | H | H | H | O | 4-Br—2-F—4-OCH(CH$_3$)$_2$—C$_6$H$_2$ | 144–149 |
| 68 | H | H | C$_2$H$_5$ | O | 4-Cl—2-F—5-OCH$_3$—C$_6$H$_2$ | Oil |

Biological examples

The damage caused to weed plants or the toleration by crop plants was assessed in accordance with a code in which the activity is expressed in numerical values from 0 to 5. These values have the following meanings:
0=no action or damage
1=0–20% action or damage
2=20–40% action or damage
3=40–60% action or damage
4=60–80% action or damage
5=80–100% action or damage 1. Action on weeds by the pre-emergence technique Seeds or pieces of rhizome of monocotyledonous and dicotyledonous weed plants were laid out in sandy loam soil in plastic pots (0=9 cm) and were covered with soil. The compounds according to the invention, formulated in the form of wettable powders or emulsion concentrates, were then applied to the surface of the covering soil as aqueous suspensions or emulsions, respectively, at various dosage rates with a water application rate equivalent to 600–800 l/hectare.

After the treatment the pots were placed in a greenhouse and were kept under good growth conditions for the weed plants (temperature 23±1° C. and relative humidity 60–80%).

Damage caused to the plants or to their emergence was assessed visually in comparison with untreated controls when the test plants had emerged after a test period of 3–4 weeks.

As the assessment values in table 2 show, the compounds according to the invention display a good herbicidal preemergence activity against a broad spectrum of weed grasses and weeds.

TABLE 2

| | Pre-emergence action | | | | |
|---|---|---|---|---|---|
| Compound Example No. | Dosage kg of active ingredient/ha | Herbicidal action | | | |
| | | SIA | CRS | ECG | LOM |
| 1 | 2.5 | 5 | 5 | 5 | 5 |
| 3 | 2.5 | 5 | 5 | 5 | 5 |
| 5 | 2.5 | 5 | 5 | 5 | 5 |
| 66 | 2.5 | 5 | 5 | 5 | 5 |
| 47 | 2.5 | 5 | 5 | 5 | 5 |
| 49 | 2.5 | 5 | 5 | 4 | 5 |

TABLE 2-continued

| | Pre-emergence action | | | | |
|---|---|---|---|---|---|
| Compound Example No. | Dosage kg of active ingredient/ha | Herbicidal action | | | |
| | | SIA | CRS | ECG | LOM |
| 5 | 2.5 | 5 | 5 | 4 | 4 |

2. Action on weeds by the post-emergence technique

Seeds or pieces of rhizome of monocotyledonous and dicotyledonous weeds were laid out in sandy loam soil in plastic pots (0=9 cm), covered with soil and cultivated under good growth conditions in a greenhouse. The test plants were treated in the trefoil stage three weeks after being sown.

The compounds according to the invention, formulated as wettable powders or as emulsion concentrates, were sprayed onto the green parts of the plants at various dosages and at a water application rate equivalent to 600 l/hectare; the action of the preparations was assessed optically in comparison with untreated controls after the test plants had spent a waiting period of approx. 3-4 weeks in a greenhouse under optimum growth conditions (temperature 23±1° C.; relative humidity 60-80%).

In the post-emergence technique too, the agents according to the invention display a good herbicidal activity against a broad spectrum of economically important weed grasses and weeds. (Table 3).

TABLE 3

| | Post-emergence action | | | |
|---|---|---|---|---|
| Compound Example No. | Dosage kg of active ingredient/ha | Herbicidal action | | |
| | | SIA | ECG | LOM |
| 1 | 2.5 | 4 | 4 | 5 |
| 3 | 2.5 | 4 | 4 | 3 |
| 5 | 2.5 | 5 | 3 | 5 |
| 66 | 2.5 | 3 | 4 | 5 |
| 47 | 2.5 | 5 | — | 5 |

TABLE 3-continued

| | Post-emergence action | | | |
|---|---|---|---|---|
| Compound Example No. | Dosage kg of active ingredient/ha | Herbicidal action | | |
| | | SIA | ECG | LOM |
| 49 | 2.5 | 4 | — | 3 |

Abbreviations:
SIA = *Sinapis alba*
CRS = *Chrysanthemum segetum*
ECG = *Echinochloa crus-galli*
LOM = *Lolium multiflorum*

We claim:
1. A compound of the formula I

$$A-NH-\underset{X}{\overset{\|}{C}}-N\diagup\diagdown\diagdown\diagup_{R^1}^{C-OR^3}_{R^2}$$

(I)

in which
X is oxygen or sulfur,
$R^1, R^2$ independently of one another are hydrogen or $(C_1-C_4)$-alkyl,
$R^3$ is hydrogen, $(C_1-C_4)$-alkyl which is unsubstituted or monosubstituted to trisubstituted by halogen, or benzyl which may be substituted up to three times by halogen, and
A is phenyl, which is unsubstituted or monosubstituted to tetrasubstituted by F, Cl, Br, $(C_1-C_4)$-alkoxy or $(C_1-C_4)$-alkoxycarbonyl-$(C_1-C_4)$-alkoxy.

2. A compound of the formula I of claim 1, wherein $R^1$ and $R^2$ are hydrogen and A is 4-halogeno-2-fluoro-5-alkoxyphenyl.

3. A compound of the formula I of claim 1, wherein the compound is 1-[N-(4-chloro-2-fluoro-5-methoxyphenyl)carbamoyl]-2-hydroxymethylpiperidine.

4. Herbicidal composition containing a herbicidally effective amount of a compound of the formula I of claim 1 and an inert carrier.

5. A process for controlling undesired plants which comprises applying a herbicidally effective amount of a compound of the formula I of claim 1 to the cultivated areas to be treated or to the plants to be treated.

* * * * *